United States Patent
Bullard

[11] Patent Number: 5,318,008
[45] Date of Patent: Jun. 7, 1994

[54] CONTROLLED TARGETING CAVITOSCOPE

[76] Inventor: James R. Bullard, P.O. Box 14727, Augusta, Ga. 30919-0727

[21] Appl. No.: 862,062

[22] Filed: Apr. 2, 1992

Related U.S. Application Data

[63] Continuation-in-part of Ser. No. 780,445, Oct. 17, 1991, which is a continuation of Ser. No. 519,440, May 4, 1990, abandoned.

[51] Int. Cl.⁵ .................................................. A61B 1/00
[52] U.S. Cl. ............................................. 128/4; 128/6
[58] Field of Search ............ 128/4, 6, 772; 138/118, 138/120, 121; 604/95

[56] References Cited

U.S. PATENT DOCUMENTS

| | | |
|---|---|---|
| 1,036,000 | 8/1912 | Pease . |
| 3,266,059 | 8/1966 | Stelle . |
| 3,802,440 | 4/1974 | Salem et al. ............ 138/120 X |
| 3,892,228 | 7/1975 | Mitsui ............................. 128/4 |
| 3,913,568 | 10/1975 | Carpenter . |
| 4,290,421 | 9/1981 | Siegmund ........................ 128/6 |
| 4,301,790 | 11/1981 | Bol et al. ........................ 128/6 |
| 4,337,761 | 7/1982 | Upsher . |
| 4,360,008 | 11/1982 | Corazzelli, Jr. . |
| 4,401,123 | 8/1983 | Baba ............................ 128/6 X |
| 4,573,451 | 3/1986 | Bauman . |
| 4,575,185 | 3/1986 | Wentzell et al. ............ 128/6 X |
| 4,620,769 | 11/1986 | Tsuno ........................... 128/6 X |
| 4,688,554 | 8/1987 | Habib ............................ 128/4 |
| 4,697,210 | 9/1987 | Toyota et al. .............. 128/4 X |
| 4,813,400 | 3/1989 | Washizuka et al. ............ 128/6 |
| 4,834,069 | 5/1989 | Umeda ............................ 128/4 |
| 4,860,644 | 8/1989 | Kohl et al. ................ 285/184 X |
| 4,919,112 | 4/1990 | Siegmund .................... 128/6 X |
| 4,947,827 | 8/1990 | Opie et al. ..................... 128/4 |
| 4,967,732 | 11/1990 | Inoue ............................. 128/4 |
| 4,986,257 | 1/1991 | Chikama ........................ 128/4 |
| 5,168,864 | 12/1992 | Shockey . |
| 5,174,277 | 12/1992 | Matsumaru . |

Primary Examiner—Richard J. Apley
Assistant Examiner—Karen A. Jalbert
Attorney, Agent, or Firm—St. Onge Steward Johnston & Reens

[57] ABSTRACT

A cavitoscope with a flexible, remotely controlled distal end permits controlled targeting of a field to be visualized within a patient. The cavitoscope incorporates a hinged distal end remotely operable by an extensible cable that pushes on the distal end to cause it to angle away from the axis of the cavitoscope.

13 Claims, 3 Drawing Sheets

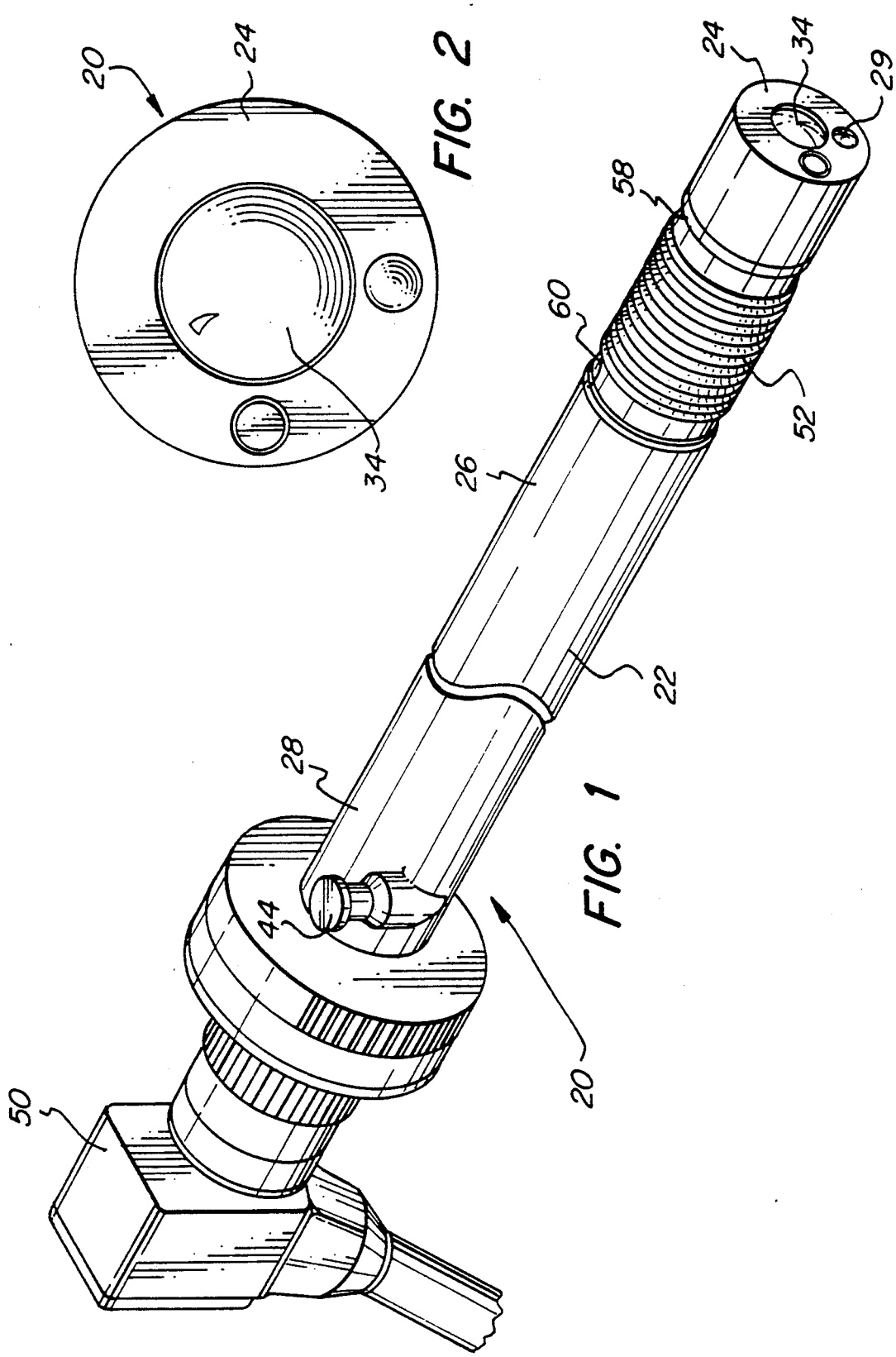

CONTROLLED TARGETING CAVITOSCOPE

This application is a continuation in part of copending U.S. patent application Ser. No. 07/780,445 filed Oct. 17, 1991 by the Applicant, James Roger Bullard, pending which is a continuation of U.S. patent application Ser. No. 07/519,440 filed May 4, 1990 by the Applicant, James Roger Bullard, abandoned.

FIELD OF THE INVENTION

The present invention relates to the field of medical optical devices permitting diagnosis and minimally invasive treatment and surgery, and more particularly, to an improved cavitoscope having a controllable targeting distal end.

BACKGROUND OF THE INVENTION

Laparoscopes are medical optical devices which are adapted for internal visualizatinn of the abdominal areas of a patient for diagnosis, treatment and surgery. A laparoscope typically consists of a rigid housing containing a series of lenses, or a bundle of optic fibers provided with a lens at their distal end, to permit viewing of the patient's internal conditions and surgical procedures from within a patient. A viewing lens is provided at the proximal end of the laparoscope housing to permit viewing of images transmitted through the optic fibers. A video camera may also be optically coupled to the viewing lens to permit display of images on a video monitor and recording of them with a video recorder. A second bundle of fibers typically are connected to a light source and extend through the laparoscope to provide illumination to the area to be visualized. The laparoscope can be augmented by providing additional instrument channels within the laparoscope housing. These additional channels may contain, for instance, forceps, cauterizing elements for controlling bleeding, and other surgical instruments. These instruments can be controlled remotely from outside the patient and their operation is viewed through the laparoscope. This permits treatment or surgery to be performed with a minimum of invasive procedures.

Certain other types of viewing instruments have been used in visualization of other areas of the body. Such instruments have included cystoscopes and uteroscopes, hysteroscopes and arthroscopes. Laryngoscopes are surgical instruments having means for indirect illumination and visualization of the pharyngeal areas of the body. U.S. Pat. Nos. 3,776,222 and 3,913,568 disclose devices for endotracheal intubation which comprise flexible or articulatable tubular probes having internal fiber optics for lighting and viewing the internal areas of the body.

Viewing instruments such as those described have generally been rigid instruments, although some flexible cystoscopes and some flexible gastroscopes have been used. Laparoscopes are typically rigid, and have a viewing field limited to the area in front of the viewing lens. It is to be appreciated that it is often very difficult to properly position even a rigid laparoscope, and it can be even more difficult with a flexible instrument. Typically the trocars established in the patient through which the laparoscope can be positioned are located only on the anterior side of the patient; therefore it is rare to obtain a complete visualization of an entire body structure. This is because the laparoscope typically permits viewing of the anterior portion of an organ, and it is difficult to look at the posterior surfaces of an organ. It is to be appreciated that it is not desirable to establish posterior trocars in a patient, and further that insertion and removal of the laparoscope is not always atraumatic, and excessive removal and excessive repositioning of a laparoscope undesirably lengthens the time required for the treatment, surgery or diagnostic procedure. Therefore visualization of posterior surfaces is not always possible. Moreover, even to obtain a partial visualization, it will be necessary to move the laparoscope, which creates a risk that it will not be possible to reestablish the initial placement of the laparoscope. The same problems apply to other optical instruments which are introduced into body cavities.

SUMMARY OF THE INVENTION

It is an object of the invention to provide a controlled targeting cavitoscope with a remotely controlled distal end. As used herein, a "cavitoscope" is a medical optical device suited for visualization of a patient's body cavities, and encompasses, for example, laparoscopcs. It is an object of the invention to provide such a cavitoscope which has an atraumatic profile and which can provide selective viewing of a field and look behind body structures.

These objects, and other objects as disclosed in this application, are achieved by a medical optical apparatus (such as a cavitoscope) having a housing with a distal end and a proximal end, and a center portion between them. The distal end is flexibly affixed to the center portion so that the distal end may be angled away from the center portion. An optical channel extends generally from the proximal end to the distal end of the housing and contains a flexible image transmitting medium with a lens at the distal end. The distal end of the housing is remotely controllable so that its movement can be precisely controlled between an unextended position and an angled position In the unextended position the distal end is retained to the center portion with the longitudinal axis of the distal end generally aligned with the longitudinal axis of the center portion. In an angled position the distal end is angled away from the longitudinal axis of the center portion. The remote control of the distal end may be achieved by providing a hinged connection between the distal end and the center portion at a peripheral edge thereof and further providing an axially extendable member at an opposite peripheral edge thereof. The axially extendable member is remotely controlled, and may comprise, for example, a cable extending through the housing. Such a cable is preferably remotely controllable by a spring returnable button. When the button is depressed, it causes the cable to extend to cause the distal end to move to an angled position. When the button is released, the cable retracts and causes the distal end to return to an aligned position with the center portion of the housing. Preferably, an expansible covering such as a flexible boot surrounds the junction between the center portion and the distal end.

Preferably, the apparatus can be rotated, either in its entirety, or only an end portion, to give a panoramic visualization.

A light channel containing a flexible light transmitting medium preferably also extends through the housing. In order to provide enough slack in the image transmitting and light transmitting media to permit the angled targeting of the distal end, a reserve length of these media should be made available in the apparatus to prevent a loss in continuity.

The apparatus of the invention permits controlled and selective visualization of a selected area through the optical channel. The present invention therefore provides a controlled targeting cavitoscope which permits viewing of a substantially larger field and with greater precision than prior art devices.

Other objects, aspects and features of the present invention in addition to those mentioned above will be pointed out in detail or will be understood from the following detailed description provided in conjunction with the accompanying drawings.

BRIEF DESCRIPTION OF THE DRAWINGS

The foregoing aspects and other features of the invention are explained in the following description, taken in connection with the accompanying drawings, wherein:

FIG. 1 is a perspective view of a controlled targeting cavitoscope in accordance with one embodiment of the invention.

FIG. 2 is an end view of the cavitoscope of FIG. 1.

DETAILED DESCRIPTION OF THE INVENTION

Figure 3:
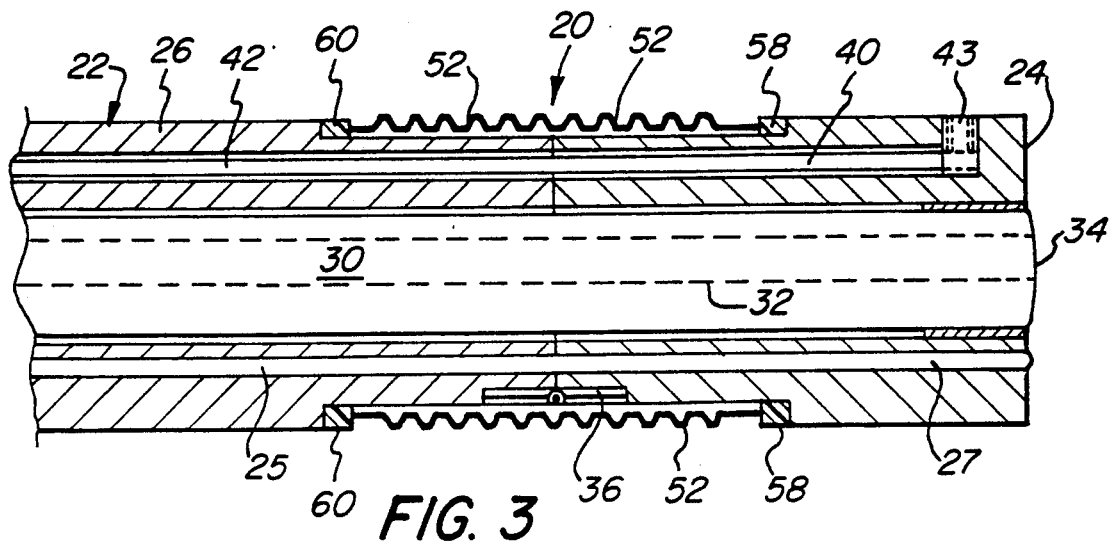
FIG. 3 is a cross-sectional view of the controlled targeting cavitoscope of FIG. 1.

Referring to FIGS. 1-5, where like numbered elements in the drawings represent the same elements, a cavitoscope 20 is shown. Cavitoscope 20 has a housing 22 and is provided with a plurality of channels therein which extend from a distal end 24 to a center portion 26 and a proximal end 28 of the cavitoscope 20.

The distal end 24 is flexibly affixed to the center portion 26 so that the distal end 24 may be angled away from the center portion 26. An optical channel 30 extends generally from the proximal end 28 to the distal end 24 of the housing 22 and contains a flexible image transmitting medium 32 (such as fiber optics) with a lens 34 at the distal end 24. A light transmitting channel 25 extends generally from the proximal end 28 to the distal end 24 and contains a light transmitting medium 27 (such as fiber optics) and is connected to a light source (not shown).

Figure 4:
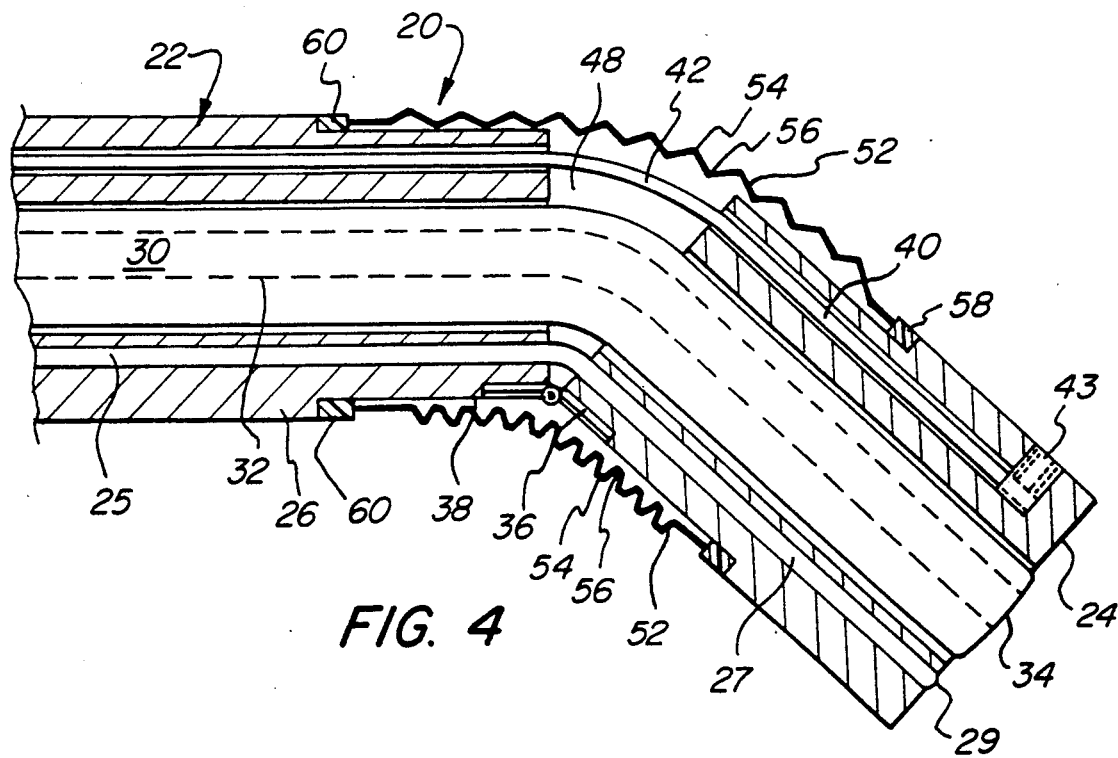
FIG. 4 is a cross-sectional view of the controlled targeting cavitoscope of FIG. 1 in an angled position.

The distal end 24 of the housing 22 is remotely controllable so that its movement can be precisely controlled between an unextended position and an angled position. In the unextended position shown in FIG. 3, the distal end 24 is retained to the center portion 26 with the axis of the distal end 24 generally aligned with the longitudinal axis of the center portion 26. In one angled position shown in FIG. 4, the distal end 24 is angled away from the longitudinal axis of the center portion 26. The remote control of the distal end 24 may be achieved by providing a hinged connection 36 between the distal end 24 and the center portion 26 at a peripheral edge 38 thereof and providing an axially extendable member 40 at an opposite peripheral edge thereof. The axially extendable member 40 is remotely controlled, and may comprise, for example, a cable 42 extending through the housing 22. Such a cable 42 is preferably remotely controllable by a spring returnable button 44. When the button 44 is depressed, it causes the cable 42 to extend to cause the distal end 24 to move to an angled position as seen in FIG. 4. When the button is released, the cable 42 retracts and causes the distal end 24 to return to its retracted position aligned with the center portion 26 of the housing 22 as seen in FIG. 3. The end 43 of cable 42 is connected to distal end 24 at a position opposite from the hinged connection 36.

The cable 42 has sufficient rigidity so as not to collapse while pushing the distal end 24. The image transmitting medium 32 is sufficiently flexible to bend and traverse the gap 48.

Optical channel 30 is provided with a flexible optical image transmitting medium 32, which is preferably a bundle of optic fibers which extend from the distal end 24 to the proximal end 28 of the cavitoscope 20. The optical image transmitting medium 32 in the optical channel 30 permits optical images to be transmitted through the optical channel 30. The viewing lens 34 on the distal end of the optical channel 30 collects optical images for transmission through the optical channel 30. The cavitoscope 20 is preferably adapted so that a video camera 50 may be mounted on the proximal end 28 of the cavitoscope 20 at the proximal end of the optical channel 30 to receive and transmit the optical images from the optical channel 30 to a television monitor (not shown) and to a video recording apparatus such as a video cassette recorder (not shown). Optical image transmitting medium 32 preferably has a reserve length in the form of a coil or other stored length which provides sufficient slack medium to permit movement of the distal end 24 without restraint created by the optical medium 32. Preferably, the reserve length is automatically retractable and storable in housing 22.

Light channel 25 is provided with the light transmitting medium 27 that permits light to be transmitted through the light channel 25. This permits the illumination of the field where treatment or diagnosis is desired. The light transmitting medium 27 is preferably a plurality of optic fibers with another suitable lens 29 at the distal end thereof as necessary. The light transmitting medium 27 is connected at its proximal end to a light source of a sufficiently high intensity to permit visualization of the field. Light image transmitting medium 27 preferably has a reserve length in the form of a coil or other stored length which provides sufficient slack medium to permit movement of the distal end 24 without restraint created by the light medium 27.

Other channels such as working channels for fluids, forceps and other instruments may also be provided. For example, a washing spray channel may be provided in the housing 22. A washing spray channel terminates at its distal end with a spray nozzle and permits delivery of a spray of irrigation liquid for washing tissue specimens during treatment or diagnosis. If a fluid channel such as a washing spray channel is provided, an inner sleeve is needed to bridge the gap 48 between fluid channel segments in housing 22 when the distal end 24 is angled away from the center portion 26 as in FIG. 4. However, in general, the cavitoscope 20 will be used primarily for viewing and will not be provided with working channels.

Figure 5:
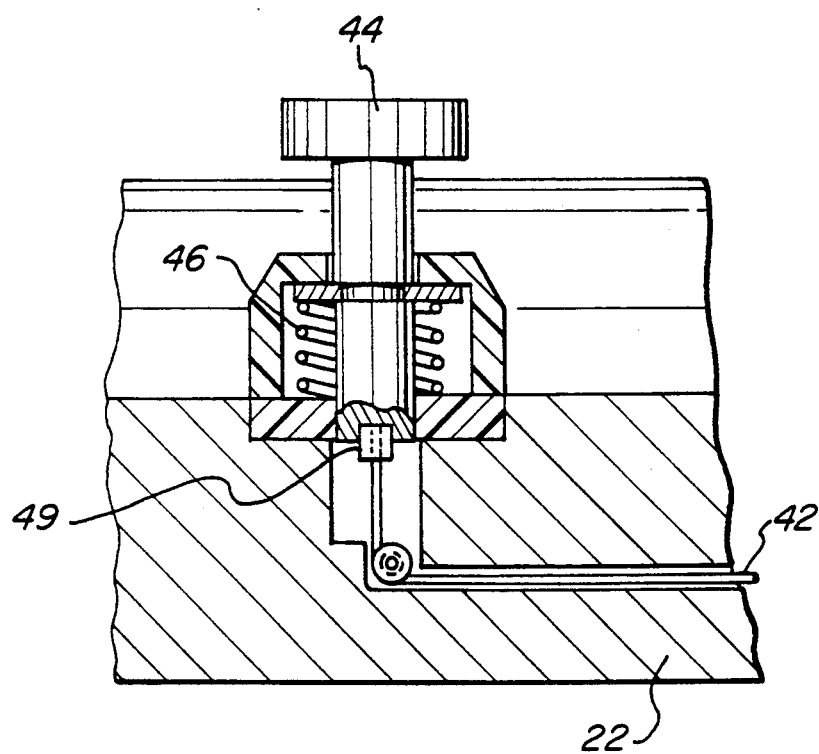
FIG. 5 is a cross-sectional view of a control button for a controlled targeting cavitoscope.

Referring now also to FIG. 5, the remote control button 44 is shown. Button 44 is biased by spring 46 and a connector 49 retains button 44 to cable 42. The spring 46 biases the button 44 in the outward position thus pulling on the cable 42. This in turn keeps the distal end 24 in its home position. When the button 44 is depressed by an operator the cable 42 is pushed forward to push on the distal end 24 and deflect it as shown in FIG. 4. Although only one type of deflection control is described above, it should be understood that any suitable type of deflection control can be used.

In the embodiment shown in FIG. 4, the distal end 24 has an angle of deflection of about 45 degrees in an inward direction. However, any suitable angle of deflection can be provided, preferably up to about 110 degrees. In addition, suitable means may be provided to deflect the distal end 24 in other than an inward direction as shown. In the embodiment shown, the length of travel of the button 44 and cable 42 limits the amount of deflection of the distal end 24. However, any suitable type of deflection limiter can be provided.

When the operator releases the button 44, the spring 46 pushes the button 44 back to its extended position. The button 44, in turn, pulls on the cable 42 which pulls on the distal end 24. This returns the distal end 24 back to its home position.

An expansible cover such as a corrugated boot 52 is generally provided to cover or seal off the gap 48 between the distal end 24 of the housing 22 and the center portion 26 thereof. The boot 52 is generally comprised of a flexible resilient material such as a polymer and has a generally tubular shape with corrugated type ridges 54 and valleys 56 between a first end 58 and a second end 60. The first end 58 of the cover 52 is provided with a retaining ring that fits snugly over the outside of the distal end 24. The second end 60 is provided with a retaining ring that fits snugly over the center portion 26. Preferably, annular channels are formed in each of the distal end 24 and center portion 26 to recess the boot 52 so that its outer surface is relatively flush with the housing 22 to minimize snagging of a trocar or other entry into the patient. The corrugations in the cover 52 are generally provided to allow the distal end 24 to move relative to the central section 26 while keeping the cover ends 58 and 60 snugly fitted to the distal end 24 and center portion 26 to prevent body fluids from entry into the cavitoscope 20.

Preferably, the cavitoscope 20 can be rotated, either in its entirety, or only an end portion, to give a panoramic visualization. Rotation of the cavitoscope 20 may be performed manually as this is achieved by rotation of the entire device about its longitudinal axis while it is located in the patent. It may be possible to also provide a hinged connection 36 and extendable member 40 in an outer sleeve that can be rotated about a central core containing the image and light transmitting media 32 and 27. In this case the manual rotation of the outer sleeve will permit panoramic viewing without requiring rotation of the video camera and related cables and equipment. The distal end 24 would then be separate from the central portion but would be retained in the outer sleeve.

In another embodiment, the distal end 24 is connected to the center portion 26 of the housing 22 by a plurality of cables located about a periphery of housing 22. Each cable extends through the housing 22 and is remotely controlled to cause the distal end 24 to move to an angled position when one or more of the cables are extended on one side of the housing 22, and to cause the distal end to return to an aligned position when the cables are uniformly retracted. Preferably there are four such cables, each of which is connected to a button 44 as prior described. In this case, the four buttons can be further provided with a single control pad, which is preferably about the size of a person's palm. The position of the cables, and thereby of the distal end 24 can be controlled using the palm sized pad that connects to all of the plurality of cables. The position of the distal end 24 can be simply and directly controlled by movement of the palm pad.

In a further embodiment, the distal end 24 is connected to the center portion 26 of the housing 22 by a plurality of actuable elements located about a periphery of housing 22. Each actuable element is remotely controlled to cause the distal end 24 to move to an angled position when one or more elements are extended on one side of the housing 22, and to cause the distal end 24 to return to an aligned position when the elements are retracted. Actuable elements may comprise hydraulically actuated pistons, or solenoid elements, or other remotely controllable elements.

The present invention provides an important and timely contribution to the art of medical devices, by providing an apparatus ideally suited to provide maximum visualization using medical optical devices such as a cavitoscope. The remotely controllable end permits a cavitoscope to view the rear surfaces of structures to give a doctor better and more complete information on a patient's condition.

It is to be appreciated that the foregoing is illustrative and not limiting of the invention, and that various changes and modifications to the preferred embodiments described above will be apparent to those skilled in the art. Such changes and modifications can be made without departing from the spirit and scope of the present invention, and it is therefore intended that such changes and modifications be covered by the following claims.

What is claimed is:

1. A medical optical apparatus, comprising:

a substantially rigid housing having a proximal end, a center portion and a distal end, said distal end of said housing being hingedly connected by a single hinge to said center portion, whereby said distal end may be angled away from an axis of said center portion;

an optical channel extending generally from said proximal end to said distal end of said housing, said optical channel having therein a flexible image transmitting medium;

an optical image input located at the distal end of said optical image transmitting medium; and at least one extendable member connected to said distal end and to said housing, said extendable member being axially movable between an unextended position to a fully extended position, said extendable member in an unextended position retaining said distal end to said center portion with an axis of said distal end generally aligned with the axis of said center portion and said extendable member in an extended position causing said distal end to be angled away from the axis of said center portion and said optical image transmitting medium to be angled flexibly therewith without a loss in continuity, said extendable member being remotely controlled to selectively permit visualization of a selected area through said optical channel; and a working channel extending from said proximal end to said distal end for providing an instrument or fluid to said distal end, said working channel being provided with an inner sleeve in a section thereof whereby a barrier is provided to define an enclosed working channel at a gap created when said distal end is angled away from the axis of said center portion of said housing.

2. A medical optical apparatus in accordance with claim 1, further comprising means for rotating said apparatus such that said apparatus may be rotated when said apparatus is established in a patient.

3. A medical optical apparatus in accordance with claim 1, further comprising a light channel extending generally from said proximal end to said distal end of said housing, said light channel having therein a flexible light transmitting medium.

4. A medical optical apparatus in accordance with claim 1, wherein said extendable member comprises a cable extending through said housing, said cable being located radially oppositely from a hinged connection between said center portion and said distal end.

5. A medical optical apparatus in accordance with claim 4, wherein said extending cable is remotely controllable by a spring returnable button, said cable extending to cause said distal end to move to an angled position when said button is depressed, and said cable retracting to cause said distal end to return to an aligned position when said button is released.

6. A medical optical apparatus in accordance with claim 1, further comprising an expansible covering surrounding a junction between said center portion and said distal end.

7. A medical optical apparatus in accordance with claim 6, wherein said expansible covering comprises a corrugated boot.

8. A cavitoscope, comprising:
a substantially rigid housing having a proximal end, a center portion and a distal end, said distal end of said housing being hingedly connected by a single hinge to said center portion, along a peripheral edge of said housing, whereby said distal end may be angled away from an axis of said center portion;
an optical channel extending generally from said proximal end to said distal end of said housing, said optical channel having therein a flexible image transmitting medium, said image transmitting medium having a reserve length;
an optical image input located at the distal end of said optical image transmitting medium;
a light channel extending generally from said proximal end to said distal end of said housing, said light channel having therein a flexible light transmitting medium, said light medium having a reserve length; and
at least one extendable member connected to said distal end oppositely from a hinged connection between said center portion and said distal end, said extendable cable member extending through said housing to said proximal end thereof, said extendable cable member being axially movable between an unextended position to a fully extended position, said extendable cable member in an unextended position retaining said distal end to said center portion with an axis of said distal end generally aligned with the axis of said center portion and said extendable cable member in an extended position causing said distal end to be angled away from the axis of said center portion and said optical image transmitting medium to be angled therewith without a loss in continuity, said extension member being remotely controlled to selectively permit visualization of a selected area through said optical channel; and
a working channel extending from said proximal end to said distal end for providing an instrument or fluid to said distal end, said working channel being provided with a barrier to define an enclosed working channel at a gap created when said distal end is angled away from the axis of said center portion of said housing.

9. A cavitoscope in accordance with claim 8, further comprising an expansible covering surrounding a junction between said center portion and said distal end.

10. A cavitoscope in accordance with claim 9, wherein said extending cable is remotely controllable by a spring returnable button, said cable extending to cause said distal end to move to an angled position when said button is depressed, and said cable retracting to cause said distal end to return to an aligned position when said button is released 11. A cavitoscope in accordance with claim 10, further comprising means for rotating such that said cavitoscope may be rotated when it is established in a patient.

12. A cavitoscope in accordance with claim 10, wherein said expansible covering comprises a corrugated boot with retaining rings for sealing against said distal end and center portion of said cavitoscope.

13. A cavitoscope, comprising:
a substantially rigid housing having a proximal end, a center portion and a distal end, said distal end of said housing being hingedly connected by a single hinge to said center portion, along a peripheral edge of said housing, whereby said distal end may be angled away from an axis of said center portion;
an optical channel extending generally from said proximal end to said distal end of said housing, said optical channel having therein a flexible image transmitting medium, said image transmitting medium having a reserve length;
an optical image input located at the distal end of said optical image transmitting medium;
a light channel extending generally from said proximal end to said distal end of said housing, said light channel having therein a flexible light transmitting medium, said light medium having a reserve length; and
at least one extendable member connected to said distal end oppositely from a hinged connection between said center portion and said distal end, said extendable cable member extending through said housing to said proximal end thereof, said extendable cable member being axially movable between an unextended position to a fully extended position, said extendable cable member in an unextended position retaining said distal end to said center portion with an axis of said distal end generally aligned with the axis of said center portion and said extendable cable member in an extended position causing said distal end to be angled away from the axis of said center portion and said optical image transmitting medium to be angled therewith without a loss in continuity, said extension member being remotely controlled to selectively permit visualization of a selected area through said optical channel;
a corrugated boot covering a junction between said center portion and said distal end, said center portion and said distal end having seats therein and annular channels therein whereby said corrugated boot is substantially flush with outer surfaces of said center portion and distal end; and a spring returnable button, said cable extending to cause said distal end to move to an angled position when said button is depressed, and said cable retracting to cause said distal end to return to an aligned position when said button is released; and a working channel extending from said proximal end to said distal end for providing an instrument or fluid to said distal end, said working channel being provided with an inner sleeve in a section thereof whereby a barrier is provided to define an enclosed working channel at a gap created when said distal end is angled away from the axis of said center portion of said housing.

* * * * *